Figure 1:
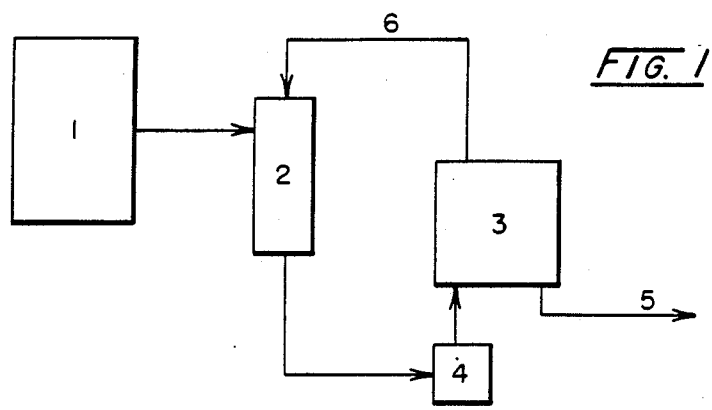

United States Patent [19]

Menicagli

[11] Patent Number: 4,894,441

[45] Date of Patent: Jan. 16, 1990

[54] PROCESS FOR THE PREPARATION OF COLLAGEN AND OBTAINED PRODUCT

[75] Inventor: Claudio Menicagli, Pisa, Italy

[73] Assignee: Istituto Gentili S.p.A., Pisa, Italy

[21] Appl. No.: 163,531

[22] Filed: Mar. 3, 1988

[30] Foreign Application Priority Data

Mar. 12, 1987 [IT] Italy .................................. 19659 A/87

[51] Int. Cl.[4] .................. C07K 15/20; C07G 7/00; A01N 63/02; B01D 13/00
[52] U.S. Cl. .................................... 530/356; 530/840; 530/842; 424/94.2; 210/636; 210/650; 210/651
[58] Field of Search ............... 424/94.2; 530/356, 840, 530/842; 210/636, 650, 651

[56] References Cited

U.S. PATENT DOCUMENTS

| | | | |
|---|---|---|---|
| 4,242,291 | 12/1980 | Hughes et al. | 530/356 |
| 4,252,759 | 2/1981 | Yannas et al. | 264/87 |
| 4,412,947 | 11/1983 | Cioca et al. | 530/356 |
| 4,488,911 | 12/1984 | Luck et al. | 530/842 |

*Primary Examiner*—Morton Foelak
*Assistant Examiner*—Carlos Azpuru
*Attorney, Agent, or Firm*—Walter H. Schneider

[57] ABSTRACT

A process for the preparation of undenaturated triple helix collagen, starting form animal tendons or cutis, by extraction with diluted organic acids, precipitation with salts, optional gelation and/or lyophilization, tangential filtration.

The obtained collagen shows favorable purity characteristics, is not allergenic and more effective in the healing processes than collagens obtained by known methods.

3 Claims, 3 Drawing Sheets

PROCESS FOR THE PREPARATION OF COLLAGEN AND OBTAINED PRODUCT

The present invention relates to a process for the preparation of collagen, starting from animal tissues, and to the pure and undenatured collagen obtained by means of said process.

Collagen is the main constituent of connective tissue and is the most abundant fibrous protein in higher vertebrates; in nature it exists as a chain arranged in a triple helical conformation, having a repeating structure.

Even though at least five main types of collagens exist in nature, the most abundant is considered to be collagen of type I, which is the main constituent of cutis, bones and tendons.

Collagen of type I, which is present in tendons, has a $\alpha 1(I)$ $\alpha 2(I)$ chain conformation, wherein $\alpha_1$ and $\alpha_2$ chains are homologues. Electrostatic interactions and hydrogen bridge bonds are present between $\alpha_1$ and $\alpha_2$ chains which, together with the presence of hydroxyproline, give strength and resistance to the molecule; the presence of said bonds, whether they are maintained in the extract, prevents the formation of a real solution, allowing at the most to obtain a gel in an acid medium, due to the swelling of the protein in the presence of water.

Collagen is at present used in various applications in medicine: in fact, it is used as a healing agent in surgical clinic, in the treatment of burns, as a vehicle and a surgical prosthesis (suture threads, gauzes, etc.), as an implant material and as a starting material for creams and ointments in the pharmaceutical and cosmetic fields.

It is therefore evident the importance of being allowed to rely on a collagen which should be as much as possible undenaturated, anallergenic and free from undesired impurities or contaminants.

The industrial processes hitherto known and used are unsatisfying in this regard, since they do not allow to attain the above mentioned ideal characteristics.

The problem is particularly urgent in case of collagen extracted from tendons, which, being of the acid insoluble type, may be hardly extracted by means of the usually followed method, based on the use of extractive solutions of inorganic salts in acetic acid or diluted hydrochloric acid, if proteolytic enzymes (papain, trypsin, kimotrypsin, pepsin) are not present. Said enzymes, even though not weakening polypeptide structure of $\alpha_1$ and $\alpha_2$ chains, cause them to unwind.

The extracted product, further, is generally cross-linked, in order to increase and improve its mechanical characteristics, to decrease its immunogenicity and to increase its resistance to organic readsorption.

This cross-linking process is generally carried out either by a physical process (U.V. light, $\alpha$ rays, X rays, $\alpha$ or $\beta$ particles, protons, electrons), or by a chemical process (formaldehyde, glutaraldehyde, acetaldehyde, pyruvic aldehyde, glyoxal, amido dialdehyde, quinones, hydroquinones, dimethylacetone, dimethylsulphone). Eventually, a final product is obtained not maintaining the structure of natural collagen.

Another problem with prior art technique, common to the extraction from both tendons and cutis, resides in the prolonged extraction times required by the dialytic purification process, to remove the salts used in the extractive step.

The process according to the present invention allows to overcome the drawbacks of the prior art, yielding a final product which is highly pure and undenaturated, since proteolytic enzymes or cross-linking agents are not used, and also more economic than that obtained by the hitherto known processes.

The process of the invention is suited for extraction of collagen from both bovine or porcine cutis and bovine tendons, which are easily available materials, being side-products from food and tanning industry.

In case of extraction from tendons, a collagen of the "acid insoluble" type is obtained in form of a gel, which may be subjected to a freeze drying process to prepare spongy tablets of the type generally used in surgical clinic.

The process of the invention consists of the following steps:

(a) extraction from the biological tissue, by means of diluted organic acids;
(b) precipitation of collagen by addition of inorganic salts;
(c) optional gelation with diluted organic acids;
(d) tangential filtration through membrane of appropriate molecular exclusion (cut-off);
(e) optional lyophilization of the final solution or gel.

Step (a) is preferably carried out using aqueous acetic acid, of concentrations ranging from 0.5 to 2 M, at a temperature not higher than 25° C., in a biological tissue: acid weight ratio from 0.1 to 0.01.

Step (b) preferably uses sodium chloride, while step (c), which takes place when the starting material consists of tendons, which give collagen of type I, insoluble in acids, is generally carried out using diluted acetic acid again.

Step (d) consists of a first washing step at constant volume and of a second concentration step. The washing step is substantially a tangential filtration process through molecular exclusion membranes, which use allows to remove a filtrate containing all of the products having a molecular weight lower than molecular exclusion of the membrane itself, independently on the nature thereof; at the same time the collagen present in the solution or gel, having a molecular weight higher than the nominal molecular exclusion of the membrane, is retained in the liquid phase which is circulated by means of a peristaltic pump. Thus, working with continuously renewed acetic acid, complete removal of all the impurities present in the starting solution or gel takes place in a short time. The gel concentration step is carried out by recycling the same gel through the tangential filtration device.

Since at each cycle liquid is removed by tangential filtration, solution or gel is consequently concentrated. The process is over when the operative pressure shown on the line manometer tends to overcome 40 p.s.i.: under such conditions, the resulting gel has a concentration comprised between 1.5 and 2%. In the case of the solution (obtained starting from cutis, which provides acid soluble collagen), the end of the operation may be indicated by viscosity measurements, hydroxyproline titre, etc., corresponding to the desired concentration.

Figure 2:
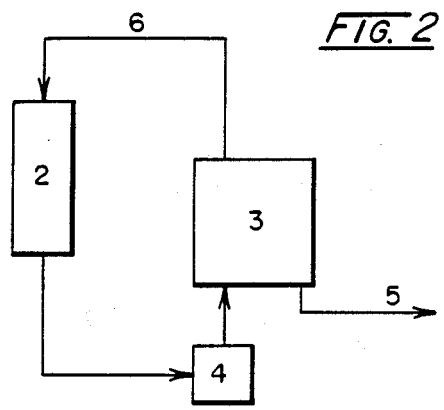

FIGS. 1 and 2, reported in the annexed drawings, show the flow chart of the above described operations: particularly, FIG. 1 reports the operative scheme of the washing at constant volume, wherein the reference number 1 is the diluted acetic acid reservoir, number 2 is the sample, number 3 is the filtrating membranes, while numbers 4, 5 and 6 are the peristaltic pump, the washing water discharge and the sample recovery, respectively.

In practice, reservoir 1 may be replaced by the same circulating acetic acid.

FIG. 2 shows the operative scheme of the collagen concentration in form of solution or gel, wherein equal reference numbers correspond to equal elements of FIG. 1. The higher exclusion limit of the used filtrating membranes is preferably from 10,000 to 100,000.

The collagen solution or gel from steps a, b and c is diluted to concentrations comprised from 0.005% to 0.5%, while the washing diluted acetic acid has a concentration from 0.01 to 1 M, preferably about 0.5 M.

When a collagen medicated with substances having a pharmacologic activity is desired, said substances may be directly dissolved or dispersed in the reservoir after removal of salts at constant volume and before concentration.

Examples of said substances particularly comprise antibiotics, vitamins, hormones and steroids. For use in gynecology, zinc sulfate is particularly preferred, for the topical treatment of herpetic affections (ovules, creams, pads etc.).

The amount of the substance to be dissolved or dispersed is calculated on the basis of multiplicative factors obtained for the subsequent concentration step of the collagen gel and solution and possibly on the basis of optional steps of transformation of the starting material.

Optional lyophilization is finally carried out according to conventional procedures.

The collagen obtained according to the process of the invention keeps its characteristic triple helix conformation, is pure, does not require any cross-linking treatment and is anallergenic.

Due to the above cited properties, the collagen of the present invention proved to be more effective in favouring the healing processes of surgical wounds and burns, allowing a natural repairing action to take place, which is favoured by the undenaturated structure itself of the obtained products.

The present invention is further illustrated by the following non-limiting examples.

EXAMPLE 1

80 g of bovine Achilles tendon were separated from fleshy and fatty portions, then frayed and minced using a mincer. The mass was washed three times with water, three times with a sodium chloride aqueous solution of concentration 1 to 10%, then with water until clear enough washing waters were obtained; each washing was carried out by decantation of the liquid.

The material was suspended in diluted acetic acid of concentration 0.1 M to 5 M, in such an amount as to have an organic material: acid ratio ranging from 0.1 to 0.01; the material was kept under mild constant stirring for 24 to 72 hrs., at a temperature not higher than 25° C.

The material was filtered through metallic mesh n. 50, collecting the liquid phase and recovering the solids; sodium chloride in an amount from 250 to 1.000 g was added to the liquid phase: collagen precipitated in form of a gummy — thready product of milky — white colour, which was separated by filtration through metallic mesh n. 40, washed with abundant distilled water and recovered. Solids were suspended again in diluted acetic acid, according to the above described procedures, and extracted again: the operations were repeated until an evident separation of collagen was obtained (about 3-4 times).

The whole resulting collagen was suspended in 5 l of 0.5 M acetic acid and kept under continue stirring until complete gelation (about 24 hrs). 500 g of sodium chloride was added to precipitate collagen, which was filtered on a metallic mesh n. 40, the solid was recovered, washed by decantation with 5 portion of distilled water (1 l each), then suspended in 0.5 l of 0.5 M acetic acid, and stirred until complete gelation (about 24 hrs.): by subsequent dilution with the same acid, 0.75 kg of 1% collagen gel (hydroxyproline titre x 7.46).

The gel was quantitatively transferred into 28/32" dialysis membranes and dyalyzed with 0.5 M acetic acid, which was continuously renewed, until sodium chloride was completely removed from gel.

The collagen gel was placed into squared trays, using a surface roll to correctly spread the very viscous mass.

The mass was pre-dried at about −40° C. for 8–10 hours, subjected to high vacuum (0.05 mm residual pressure) for 16 hrs, then temperature was raised at costant speed (about 2° C.hour) until the product reached 30° C.

The material was finally heated to 40° C. for 2 hrs; the lyophilized film was cooled and divided by means of semi-manual shear.

The resulting product has the following characteristic and constant chemico-physical parameters.

Chemical parameters (a) Hydroxyproline content, spectrophotometrically determined, higher than 13% and — anyway — not lower than 12%.

(b) total nitrogen content, determined according to Kjeldhal method, higher than 17.5%, and — anyway — not lower than 16.2%.

(c) residual humidity content lower than 20%.

Physical parameters (a) Immersion time per weight unit not lower than 15 min.

(b) water absorption coefficient per weight unit not lower than 25 g.

(c) tear resistance not lower than 2000 g/cm$^2$.

(d) wrinkling temperature from 90 to 120° C.

(e) Pepsine digestion time in N/10 HCl (1/1 weight ratio) not lower than 20 min.

EXAMPLE 2

The gel obtained in the above example was divided into 3 lots and diluted with 0.5 M acetic acid, to concentrations of 0.1, 0.2 and 0.3% by weight, before the lyophilization step.

Salting off was then carried out, according to the operative schemes of FIGS. 1 and 2, using 0.5 M acetic acid and membrane having an exclusion limit of 30.000.

Figure 3:
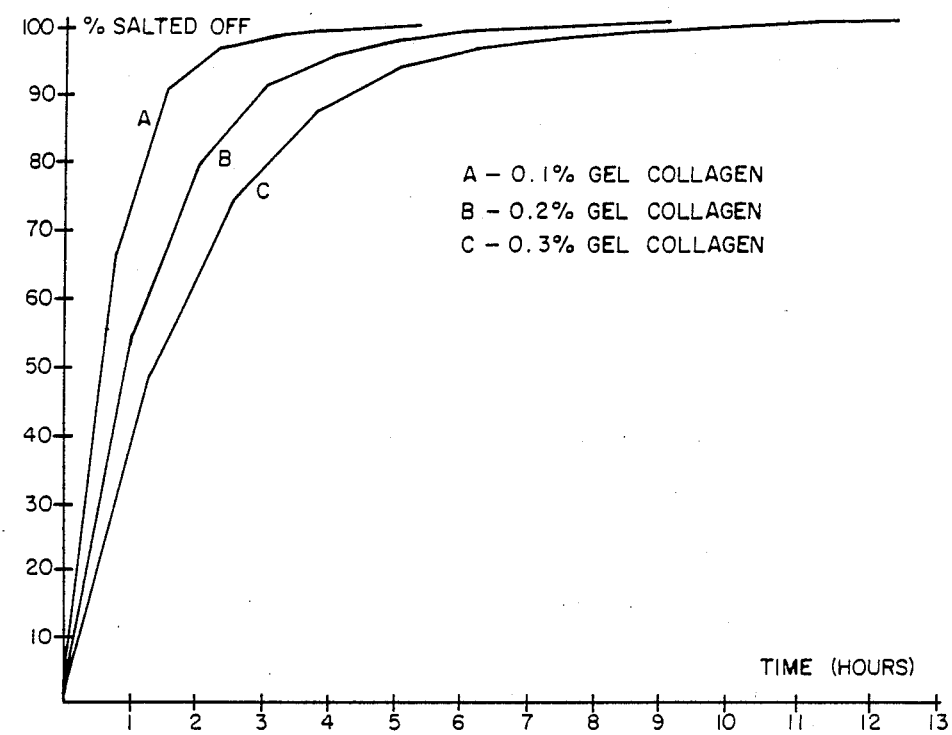

The typical proceeding of process, for 1 liter of collagen gel of concentrations 0.1 -0.2 and 0.3%, is represented in FIG. 3, which shows the percentage saline content change in the filtered liquid, versus time; the sample has 100% purity when 100% of filtered saline content is attained.

The described process relates to a collagen gel having 0.1 - 0.2 and 0.3% concentration, containing sodium chloride, but it can be applied to any saline impurity in collagen gel or solution, as reported in FIG. 3 as percentage salting off versus time; moreover, the above stated basic principles may be applied to the various concentrations: of course the characteristic curves of the process will vary case by case.

Figure 4:
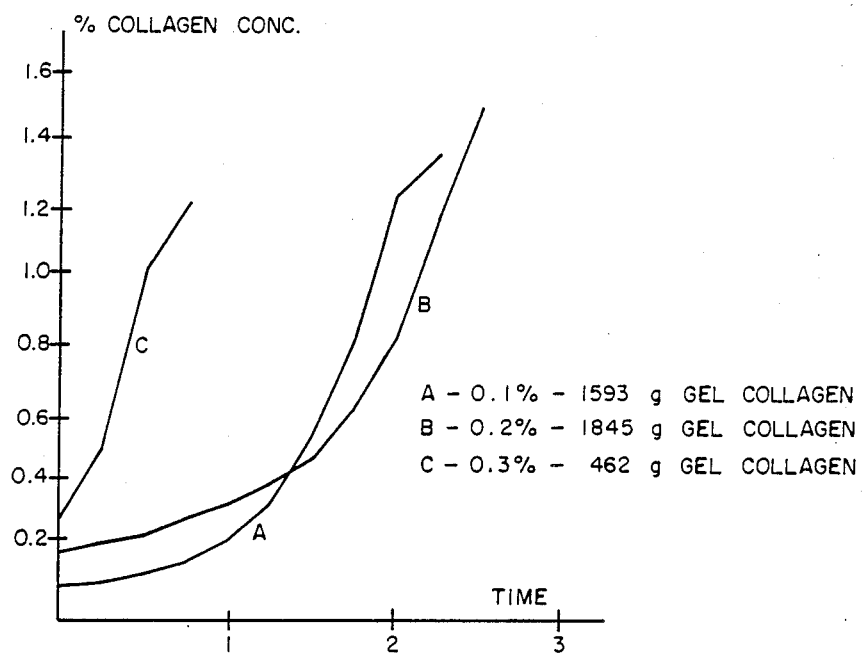

FIG. 4 shows the proceeding of the concentration step for collagen gel having a different concentration (0.1, 0.2 and 0.3%).

The basic principle of the process may be applied to collagen gels or solutions of varying concentration also in this case; the process ends when collagen concentration (hydroxyproline titre x 7.46) reaches the present value.

Filtrating membranes regeneration is carried out with 0.5 M acetic acid. It should be pointed out that the characteristic proceeding of the curves reported in Table 4, and more generally of the process, is also affected by the amount of the starting sample.

I claim:

1. A process for treating bovine tendon to extract high purity collagen in the form of a viscous gel, said extracted collagen having the triple helix configuration of natural collagen and being suitable for direct use in surgical sponges and the like, said extraction being effected without the use of an enzymatic treatment to solubilize the collagen and said extracted collagen not being subjected to a cross-linking procedure to modify its structure, which comprises: suspending a finely divided mass of bovine tendon in a 0.5-14 2.0 M aqueous acetic acid solution in an amount to provide a bovine tendon/acid weight ratio of 01-0.01/1; mildly agitating the resultant suspension for a period of 24-72 hrs. at a temperature not exceeding about 25° C.; separating the suspended solid phase and precipitating collagen from the liquid phase by the addition thereto of sodium chloride, said precipitated collagen being in the form of a gummy, thready product of milky white color; separating said precipitated collagen and suspending it in acetic acid and agitating until complete gelatin is obtained; diluting the resultant collagen gel to a concentration of 0.005-0.5% and subjecting it to tangential filtration through a molecular exclusion membrane having an exclusion limit of 10,000-100,000 using acetic acid of 0.01-1.0 M whereby a filtrate containing impurities of molecular weight below the exclusion is removed while the collagen gel is retained recycling the collagen gel through tangential filtration until all impurities are removed; recovering and drying the purified collagen gel and lyophilizing the same.

2. Collagen suitable for use in surgical sponges and the like recovered from bovine tendon according to the process of claim 1.

3. A pharmaceutical composition comprising collagen recovered from bevine tendon ccording to the process of claim 1 in combination with other constituents having pharmaceutical activities.

* * * * *